(12) United States Patent
Jensen et al.

(10) Patent No.: US 12,208,277 B2
(45) Date of Patent: Jan. 28, 2025

(54) LASER HEAD AND LASER PROBE FOR LOW-LEVEL LASER THERAPY AND A METHOD OF CONTROLLING SUCH LASER PROBE

(71) Applicant: Akeda Sp. z o.o., Szczecin (PL)

(72) Inventors: Henrik Ljungberg Jensen, Jelling (DK); Leif Kvist Pedersen, Lystrup (DK); Svend Prosch-Jensen, Horsens (DK)

(73) Assignee: Akeda Sp. z o.o., Szczecin (PL)

( * ) Notice: Subject to any disclaimer, the term of this patent is extended or adjusted under 35 U.S.C. 154(b) by 0 days.

(21) Appl. No.: 17/271,589

(22) PCT Filed: Aug. 28, 2019

(86) PCT No.: PCT/DK2019/050249
§ 371 (c)(1),
(2) Date: Feb. 25, 2021

(87) PCT Pub. No.: WO2020/043253
PCT Pub. Date: Mar. 5, 2020

(65) Prior Publication Data
US 2021/0244961 A1   Aug. 12, 2021

(30) Foreign Application Priority Data
Aug. 30, 2018   (DK) .......................... PA 2018 70556

(51) Int. Cl.
*A61N 5/00*    (2006.01)
*A61N 5/06*    (2006.01)
*A61B 18/20*   (2006.01)
*A61N 5/067*   (2006.01)

(52) U.S. Cl.
CPC ...... *A61N 5/06* (2013.01); *A61B 2018/20553* (2017.05); *A61N 2005/005* (2013.01); *A61N 2005/0626* (2013.01); *A61N 2005/0652* (2013.01); *A61N 5/067* (2021.08)

(58) Field of Classification Search
None
See application file for complete search history.

(56) References Cited

U.S. PATENT DOCUMENTS

| | | | |
|---|---|---|---|
| 6,572,637 B1* | 6/2003 | Yamazaki | A61B 18/20 606/9 |
| 2006/0095098 A1* | 5/2006 | Shanks | A61N 5/0616 606/13 |
| 2006/0129140 A1* | 6/2006 | Todd | G06K 17/00 606/1 |

(Continued)

FOREIGN PATENT DOCUMENTS

| | | |
|---|---|---|
| CN | 107872967 A | 4/2018 |
| EP | 2 753 261 A1 | 7/2014 |

(Continued)

*Primary Examiner* — Sana Sahand
(74) *Attorney, Agent, or Firm* — Dykema Gossett PLLC (57) ABSTRACT

Aspects of the present disclosure are directed to, for example, a method of changing operational parameters of a laser probe. The method including the steps of recognising a connection pattern between the laser probe and a battery, setting the laser probe in a programmable mode, and receiving instructions for changing the operational parameters of the laser probe.

6 Claims, 9 Drawing Sheets

(56) References Cited

U.S. PATENT DOCUMENTS

| | | |
|---|---|---|
| 2007/0060984 A1 | 3/2007 | Webb et al. |
| 2008/0125835 A1 | 5/2008 | Laurent |
| 2011/0040358 A1* | 2/2011 | Bean ................ A61B 18/24 |
| | | 607/89 |
| 2012/0197357 A1 | 8/2012 | Dewey et al. |
| 2013/0035746 A1 | 2/2013 | Bouboulis |
| 2013/0197495 A1 | 8/2013 | Koifman et al. |
| 2014/0214136 A1 | 7/2014 | Liu et al. |
| 2015/0112411 A1 | 4/2015 | Beckman et al. |
| 2018/0008839 A1 | 1/2018 | Hamid |

FOREIGN PATENT DOCUMENTS

| | | |
|---|---|---|
| EP | 3009081 A | 4/2016 |
| WO | 2004075721 A2 | 9/2004 |
| WO | 2011047149 A1 | 4/2011 |
| WO | 2014072821 A2 | 5/2014 |
| WO | 2018097428 A2 | 5/2018 |

* cited by examiner

Prior art

LASER HEAD AND LASER PROBE FOR LOW-LEVEL LASER THERAPY AND A METHOD OF CONTROLLING SUCH LASER PROBE

CROSS-REFERENCE TO RELATED APPLICATIONS

This application is a national stage filing based upon International PCT Application No. PCT/DK2019/050249, filed 28 Aug. 2019, which claims the benefit of priority to Denmark application No. PA 2018 70556, filed 30 Aug. 2018.

FIELD OF THE INVENTION

The present invention relates to a low-level laser therapy (LLLT) laser probe and especially a laser head for increasing the efficiency of heat removal and a laser diode for decreasing heat production and increasing the efficiency of the laser probe.

The present invention also relates to a method for changing the operational parameters of a laser probe for low-level laser therapy.

BACKGROUND OF THE INVENTION

Low-level laser therapy (LLLT) is a growing market where lasers or light-emitting diodes are used for pain relief, healing of tissues, inflammation, ulcers, skin disorders, acupuncture, zone therapy, immune therapy and, in general, activation of the immune system.

At present, the laser probe used in low-level laser therapy is connected by a cord to a power supply due to the high energy demand of the laser probe. The power supply makes the entire system heavy and not easily moveable. The heavy system makes the use of laser probes in private households less attractive.

Furthermore, the cord can be a source of irritation when working around the human body.

There is a need for a more efficient laser probe for LLLT, thereby enabling the laser probe to be powered by a battery having a size allowing the battery to be attached directly to the laser probe, such that the laser probe can be cordless.

Furthermore, a present day laser probe has an inefficient internal heat removal which causes the laser probe to often have a temperature that damages the one or more laser diodes. At present, this problem is solved by letting the laser probe cool or by changing the laser head.

Thus, the user is forced to have a longer treatment time or to have a series of extra laser heads.

This is also a limiting factor in the adoption of the laser probes in private households, because private household users are not experts and will typically not have more than one laser head and also may not follow the instructions.

The heat generation also prevents the use of the laser probe inside the human body, such as oral treatment, anal treatment and vaginal treatment as the temperature near the laser diodes can be over 37 degrees or 50 degrees Celsius or even higher.

Thus, there is a need for a more efficient heat removal system for increasing the operational time of the laser probe and/or for increasing the lifetime of the laser diode.

The laser probe may be used in therapeutic and non-therapeutic methods, such as pain relief healing of tissues, inflammation, ulcers, skin disorders and in general activation of the immune system. In all cases, the requirements for hygiene are strict and the laser probe must comply with these requirements.

At present, a laser probe is connected by a cord to a power supply. The power supply may be adapted such that the user can control the operational parameters of the laser probe at the power supply. The operational parameters could be power of the laser, treatment time and/or repetition rate of a beep sound.

This is not possible if the laser probe is cordless. The laser probe could in theory be equipped with buttons, but having buttons on the laser probe would reduce the level of hygiene as it is hard to clean buttons properly. This could be a source for infections.

Thus, there is a need for a method that can change the operational parameters of the laser probe without the use of buttons.

OBJECT OF THE INVENTION

It is an object of the invention to provide a laser probe having an efficient heat removal.

It is an object of the invention to provide an efficient laser probe for low-level laser therapy where the laser probe can be powered by a battery attached to the laser probe, thereby making it cordless.

It is another object of the invention to provide a laser probe that meets a high hygienic standard.

DESCRIPTION OF THE INVENTION

The embodiments of the laser probes described in this document may be of any laser class, especially laser class 3B or laser class 4.

Both laser class 3B and 4 can provide enough energy to heat tissue, however there is a risk of a burn due to heat generated in the tissue if the laser light is greater than 500 $mW/cm^2$.

The embodiments of the laser probes described in this document may emit light in the range of 600-1000 nm. The range is also called the biological window as these wavelengths can penetrate the skin and affect the cells.

An object of the invention is provided by a laser head for a low-level laser therapy (LLLT) laser probe.

The laser head may comprise an outer cap and an inner cap connected to the outer cap and positioned partly within the outer cap, thereby forming a heat channel having an exhaust in-between the caps.

The outer cap may have a downwardly extending outer skirt along or near an outer periphery. Thereby, the outer cap may have a U-shaped cross-section.

The inner cap may have a downwardly extending inner skirt along or near an inner periphery. Thereby, the inner cap may have a U-shaped cross-section.

The skilled person would know how to connect the outer and inner cap, such that a heat channel having an exhaust is formed. The heat channel will make it possible to remove heat by convection, thereby increasing the heat removal.

The outer cap may comprise one or more bores for one or more laser diodes.

Each bore may be adapted for holding one or more lenses in front of a laser diode, such that the beam profiles can be either focused towards a common focal point or spread out.

By having a common focal point, each laser diode may generate a part of the emitted light needed for a wanted effect, and thus less heat will be generated at each diode.

The heat generated is spread over a larger area, thereby keeping the temperature lower. The efficiency of a laser diode decreases with temperature and likewise the lifetime of a laser diode is temperature dependent, where higher temperatures causes a shorter lifetime.

Each lens may be a fibre rod, window or a lens for focusing the laser light, or a lens for spreading the laser light.

The inner cap may be adapted for enabling each laser diode to be connected to power through the inner cap. Thus, the inner cap may have punctures for accommodating pins from each laser diode.

The skilled person would know how to connect the one or more laser diodes to power.

The inner cap may comprise a neck connection part for interlocking with a body of a laser probe.

The inner cap may be adapted for forming an inlet channel having an intake between the inner cap and the body when the inner cap is connected to the body.

The inner cap may comprise a centrally positioned ventilator for creating a flow from the inlet channel through the heat channel.

The effect of the ventilator is that a flow is created which will increase the heat removal from the one or more laser diodes, and thus the temperature of the one or more laser diodes is decreased. This will enable the laser probe to be used for longer time periods.

Furthermore, the reduced temperature will increase the lifetime of the laser diodes.

The flow may be a turbulent flow, as the turbulent flow will increase the heat removal compared to a laminar flow. The ventilator can make the flow more turbulent by forcing more air through the heat channel.

The ventilator forcing air from the inlet channel through the heat channel decreases the need for passive cooling. Thus, the laser head can be made more compact, which decreases the overall weight of the laser probe and enables a user to use the laser probe for longer periods of time without tiring or getting shoulder injuries.

Furthermore, the laser head can be made more hygienic as the need for cooling grooves are removed. Cooling grooves are well-known for collecting grime.

The neck connection part may be threaded, or be a plug or a socket.

The skilled person would know how to adapt the inner cap, such that an inlet channel having an intake is formed between the inner cap and the body of a laser probe.

The inner cap may comprise means for electrically connecting the laser head with a controller and/or with power.

The laser head may comprise one or more laser diodes. The one or more laser diodes may emit light in the range of 600-1000 nm which is suitable for low-level laser therapy.

In an embodiment of a laser head for a low-level laser therapy (LLLT) laser probe. The laser head comprises an outer cap and an inner cap. The inner cap is connected to the outer cap and the inner cap is positioned partly within the outer cap. Thereby, the inner and outer cap form a heat channel which has an exhaust in-between the caps. The outer cap comprises one or more bores for one or more laser diodes. The inner cap comprises a neck connection part for interlocking with a body of a laser probe. The inner cap and the body form when connected an inlet channel which have an intake. The inner cap further comprises a centrally positioned ventilator for creating a flow from the inlet channel through the heat channel.

The embodiment of the laser head has such efficient heat removal that the laser head may be used inside the human body, e.g. for oral treatment, anal treatment and vaginal treatment.

In an aspect of the invention, the outer cap and the inner cap may be positioned such that the exhaust encloses the ventilator.

In an embodiment the inner cap is positioned within the outer cap while keeping a distance to outer cap.

The exhaust may be ring-shaped thereby enclosing the ventilator within.

When in use, the exhaust may be blocked or partly blocked by the user's hand. This problem is solved by having an exhaust enclosing the ventilator, such that air may flow out of the laser head in all directions. Thereby, the exhaust and heat channel cannot be completely blocked.

Furthermore, the one or more laser diodes will heat the laser head and especially the outer cap which is in direct contact with the one or more laser diodes. Thus, heat will dissipate in all directions from the laser head. By having an exhaust enclosing the ventilator it is ensured that air will dissipate over a large area.

In an aspect of the invention, the inner cap is adapted such that the intake encloses the ventilator.

The intake may be ring-shaped thereby enclosing the ventilator within.

When in use, the intake may be blocked or partly blocked by the user's hand. This problem is solved by having an intake enclosing the ventilator, such that air may be sucked in by the ventilator from all directions. Thereby, the intake and inlet channel cannot be completely blocked.

Furthermore, the ventilator may suck air from a relatively large area, thereby increasing the overall flow.

In an aspect of the invention, the exhaust and the intake may be offset relatively to each other such that the amount of recirculated air is reduced.

This will increase the heat removal as there will be a larger temperature gradient between the air and the laser head.

In an aspect of the invention, the one or more bores go through the outer cap.

Thereby, a housing of a laser diode inserted in a bore may be in direct contact with the heat channel. This enables heat to be removed directly from the heat-generating laser diode making the heat removal more efficient.

Likewise, this will lower the temperature of the one or more laser diodes, thereby prolonging the lifetime of the one or more laser diodes.

In an aspect of the invention the outer cap may have a cone facing the ventilator.

The cone will direct the air flow in all directions, thereby ensuring that the air flow is distributed relatively evenly to all parts of the heat channel. This will reduce the change of airflow dead zones.

Thus, the cone increases the heat removal.

In an aspect of the invention, the outer cap may be made of a heat-conducting material.

The outer cap is in direct contact with the heat-generating one or more laser diodes. Thus, the heat-conducting material can spread the generated heat over a large area along the heat channel. This will increase the efficiency of the heat removal.

The heat-conducting material could be a metal such as copper or aluminium. Both copper and aluminium have good heat-conducting characteristics.

The outer cap may be made of thermal plastic.

The inner cap may be made of heat-conducting material such as thermal plastic or copper or aluminium.

In an aspect of the invention, the ventilator may be a mini-fan. The mini-fan is an efficient and small fan, which is capable of being installed into the laser head, while being able to cause the airflow to create turbulence within the heat channel.

An object of the invention is achieved by a laser diode for a low-level laser therapy (LLLT) laser probe.

The laser diode may comprise an emitter, a housing for protecting the emitter having a window for emission of light, and pins connected to the emitter.

The laser diode may further comprise an insert lens positioned within the housing between the emitter and the window for adjusting beam divergence.

A laser diode usually emits laser light in an angle of 10×30 degrees. This makes it hard to utilize the laser diode without a considerable loss in energy. In theory the loss can be prevented by positioning a lens right in front of the laser diode; however this is rarely possible.

In the case of laser probes for low-level laser therapy, the lens is typically positioned at a distance of 10-15 mm from the laser diode. This may lead to a loss of the laser light which can be up to 40%. This decreases the efficiency of the laser probe and increases the heat generation, both of which are unwanted effects.

As an example, if 1 W of laser light is needed from the laser probe, then the one or more laser diodes must produce 1.67 W of laser light if the loss is 40%. The 0.67 W of laser light will be converted to heat in the laser head which must be removed.

The effect of the insert lens is that the angle of the beam can be adjusted such that the loss of laser light is removed. This will increase the efficiency of the laser probe significantly, and furthermore the heat generated is reduced significantly.

The insert lens will, in some cases, enable the laser probe to be passively cooled.

This will likewise put less strain on the ventilator of the laser head described above, which will further increase the efficiency of the laser probe as a whole.

In an aspect of the invention, the insert lens may be made of glass or plastic.

Glass optics are preferred at high energy, because plastic optics can melt if an impurity is positioned on the surface of the optics.

The insert lens may be coated or uncoated.

A Fresnel insert lens may be used.

An object of the invention is achieved by a laser probe for low-level laser therapy.

The laser probe may comprise a laser head including one or more laser diodes for providing laser light.

The laser head may further include one or more lenses for spreading or focusing the laser light.

Each lens may be a fibre rod or a converging lens for focusing the laser light or a diverging lens for spreading the laser light.

The laser probe may comprise a loudspeaker for informing the user when to move the laser probe.

The laser probe may comprise a controller for controlling different operational parameters of the laser probe, such as power of the laser light, treatment time and/or repetition rate of a loudspeaker providing a sound, for example once every 10 seconds.

The laser probe may comprise a body, which may function as a handle.

The body may be adapted for mechanical connection with a battery and/or a laser head.

The controller may comprise a first connector for connecting with the laser head and a second connector for connection with a battery.

The control may be positioned within the body.

The controller may control the functions of the laser probe such as power, ventilator speed, treatment time, etc.

This laser probe may be used in therapeutic and non-therapeutic methods, such as pain relief healing of tissues, inflammation, ulcers, skin disorders, acupuncture, zone therapy and immune therapy and in general activation of the immune system.

In an aspect of the invention, the laser probe may have one or more laser diodes, wherein at least one laser diode may comprise an emitter, a housing for protecting the emitter having a window for emission of light, pins connected to the emitter and an insert lens. The insert lens is positioned within the housing between the emitter and the window for adjusting beam divergence.

In an aspect of the invention the laser probe has a laser head for a low-level laser therapy (LLLT) laser probe. The laser head comprises an outer cap and an inner cap. The inner cap is connected to the outer cap, and the inner cap is positioned partly within the outer cap. Thereby the inner and outer cap form a heat channel which has an exhaust in-between the caps. The outer cap comprises one or more bores for one or more laser diodes. The inner cap comprises a neck connection part for interlocking with a body of a laser probe. The inner cap and the body form, when connected, an inlet channel that has an intake. The inner cap further comprises a centrally positioned ventilator for creating a flow from the inlet channel through the heat channel.

The laser head enables the laser probe to be used inside the human body, e.g. for oral treatment, anal treatment and vaginal treatment as the temperature.

Furthermore, the intake and the exhaust have a general direction facing away from the treated patient, because the exhaust would otherwise cool the patient due to convection.

A laser probe having both a laser head as described above and a laser diode with an insert lens described above eliminates the heat problems known from the prior art. Thereby, the user may use the laser probe without a risk of overheating the laser diodes.

In an aspect of the invention, the laser probe may comprise a battery connected to the second connector.

In an aspect of the invention, the laser probe comprises one or more converging lenses which have a common focal point.

The common focal point may be 1.25-1.75 cm or 1.5 cm from the lenses. This would cause the laser beam or laser beams to be strongly divergent past the common focal point, thereby making the laser probe eye-safe as the intensity decreases quickly with distance from the common focal point.

This enables the laser probe to be used without the user having to wear safety glasses. This will further enable the adoption of LLLT in private households as the laser probe is eye-safe.

An object of the invention is achieved by a method of changing operational parameters of a laser probe.

The method may comprise an act of recognising a connection pattern between the laser probe and a battery.

The connection pattern between the laser probe and a battery could be connection, disconnection, connection.

So if a user first connects a laser probe to a battery, then disconnects the laser probe and the battery, and within a time period reconnects the laser probe to the battery, then this connection-disconnection-connection pattern will be recognised and cause an act of setting the laser probe in a programmable mode.

The laser may be in a CW (continuous wave)-mode or in a pulsed mode.

When the laser probe is in a programmable mode, the operational parameters may be changed. The operational parameters may be laser power or treatment time or repetition rate of a notification sound or a laser pulse repetition rate.

The laser pulse repetition rate may be between 1-10,000 Hz.

The laser power may be between 0-100%.

The treatment time can be from seconds to hours.

The method may comprise an act of receiving instructions for changing the operational parameters of the laser probe.

The laser probe may receive instructions wirelessly, thereby causing a change in the operational parameters of the laser probe.

The laser probe may comprise sets of preset operational parameters.

The laser probe may receive instructions by the user repeating the connection pattern, thereby shifting between the sets of preset operational parameters. Thereby, the user may change the operational parameters using only the laser probe and the battery.

The method enables the user to control a laser probe without the use of any buttons.

Thus, a laser probe capable of performing the method may be made without any buttons, thereby hygiene is increased.

In an embodiment, the laser probe may comprise sets of preset operational parameters. The method of changing operational parameters may cause the laser probe to switch between the sets of preset operational parameters, when the method repeatedly recognises the connection pattern.

The method enables the user to control a laser probe without the use of any buttons. Thus, a laser probe capable of performing the method may be made without any buttons, thereby hygiene is increased.

The method may comprise an act of pairing the laser probe with a remote via Bluetooth™. Bluetooth™ is a short-range wireless technology standard that is used for exchanging data between fixed and mobile devices over short distances.

The Bluetooth™ function may be approved for R&TTE Directive 1999/5/EC Essential Requirements for Health and Safety.

The method enables the user to control a laser probe without the use of any buttons. Thus, a laser probe capable of performing the method may be made without any buttons, thereby hygiene is increased.

An object of the invention is achieved by a laser probe for low-level laser therapy. The laser probe may comprise a controller adapted to measure a connection between the laser probe and a battery.

If a user connects the laser probe to a battery, then the laser probe will be set in an on-mode and begin to generate a laser beam as determined by the operational parameters of the laser probe, such as laser power, laser on-time and/or laser off-time.

If a user disconnects the laser probe and the battery, then the laser probe loses power and the laser is set in an off-mode.

If a user first connects a laser probe to a battery, then disconnects the laser probe and the battery, and within a time period reconnects the laser probe to the battery, then the controller will measure this as a change in voltage as a function of time. If this change corresponds to the connection pattern, then the controller will recognise the pattern and perform an act setting the laser probe in a programmable mode.

Afterwards, the laser probe will perform an act of receiving instructions for changing the operational parameters of the laser probe.

The user may provide the instructions wirelessly or by repeating the connection pattern, thereby shifting between sets of preset operational parameters.

The operational parameters may be laser power or treatment time or repetition rate of a notification sound. The notification sound will provide the user with information of when to change position of the laser probe.

The laser probe may have means adapted to execute the acts of changing operational parameters of a laser probe.

The controller may comprise a Bluetooth™ device adapted to perform an act of pairing the laser probe with a remote via Bluetooth™.

The remote may be a laptop or smart phone or tablet or any other device capable of pairing with the controller and sending instructions to the laser probe.

An object of the invention is achieved by a computer program comprising instructions to cause the laser probe to execute the acts of the method of changing operational parameters of the laser probe.

An object of the invention is achieved by a computer-readable medium on which the computer program is stored.

| | |
|---|---|
| Laser probe | 10 |
| Body | 20 |
| First connector | 22 |
| Second connector | 24 |
| Controller | 30 |
| Bluetooth device | 32 |
| Laser head | 40 |
| Outer cap | 42 |
| Bores | 46 |
| Cone | 48 |
| Inner cap | 50 |
| Heat channel | 60 |
| Exhaust | 62 |
| Inlet channel | 64 |
| Intake | 66 |
| Ventilator | 70 |
| Flow | 72 |
| Laser diodes | 80 |
| Housing | 82 |
| Window | 84 |
| Pins | 86 |
| Emitter | 88 |
| Insert lens | 90 |
| Battery | 100 |
| Operational parameters | 110 |
| Connection pattern | 120 |
| Programmable mode | 130 |
| Remote | 140 |
| Skin | 200 |
| Penetration depth | 210 |
| Method of changing operational parameters of a laser probe | 1000 |
| Act of recognising | 1100 |
| Act of setting | 1200 |
| Act of receiving | 1300 |
| Act of pairing | 1400 |

DETAILED DESCRIPTION OF THE INVENTION

Figure 1:
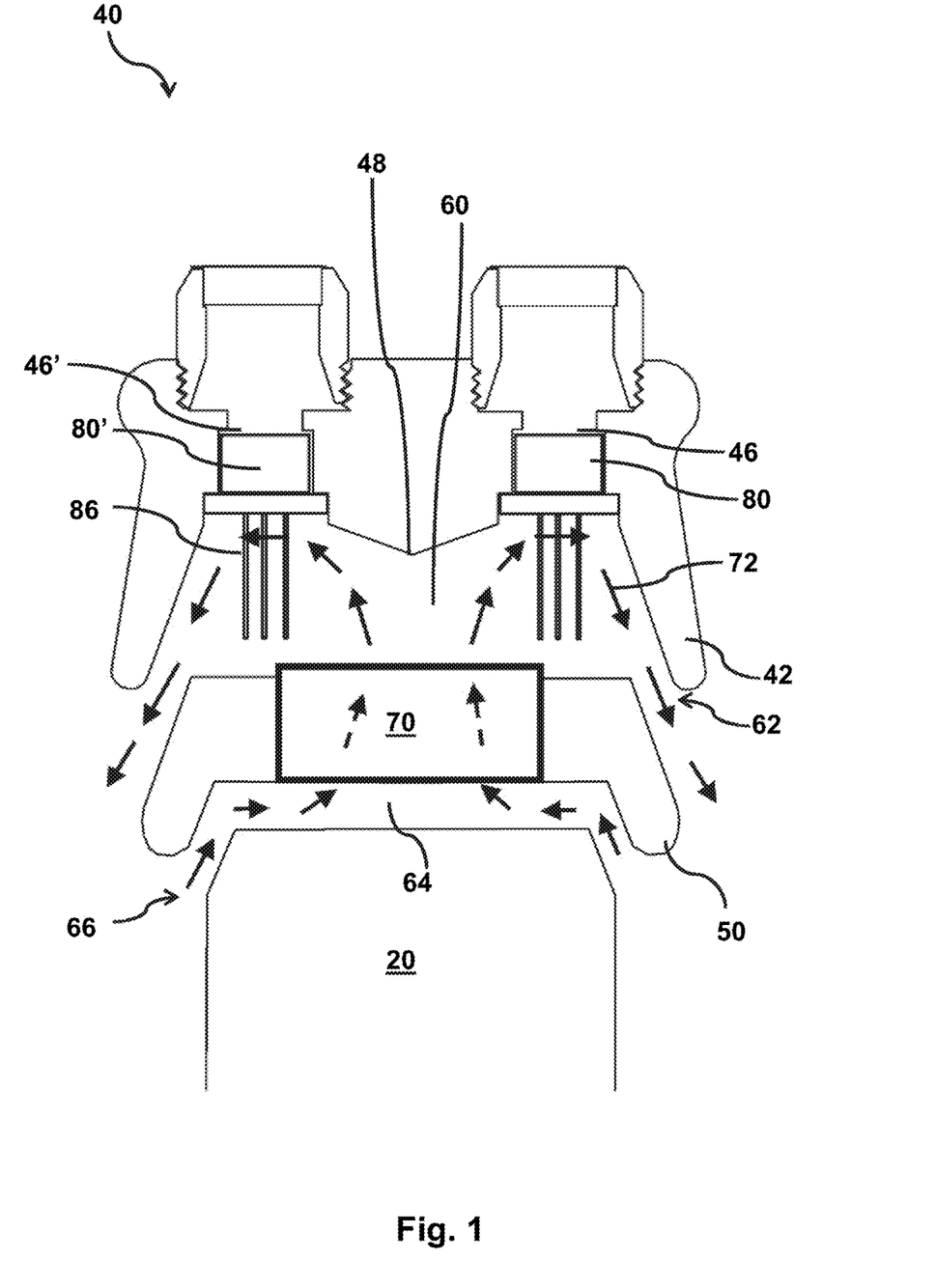
FIG. 1 illustrates a cross-sectional view of a laser head.

FIG. 1 illustrates a cross-sectional view of a laser head 40 for a low-level laser therapy (LLLT) laser probe 10 (not shown).

The laser head 40 comprises an outer cap 42 and an inner cap 50 connected to the outer cap 42 and positioned partly within the outer cap 42, thereby forming a heat channel 60 having an exhaust 62 in-between the caps 42, 50.

The outer cap 42 comprises two bores 46, 46' for the two laser diodes 80, 80'.

The pins 86 of each laser diode 80, 80' are connected through the inner cap 50, such that the laser diodes 80, 80' can be powered.

Each bore 46, 46' has a threaded part for holding a lens in front of the laser diode 80, 80'.

The inner cap 50 comprises a not shown neck connection part for connection with a laser probe body 20.

The inner cap 50 and the laser probe body 20 form an inlet channel 64 having an intake 66 formed in-between the inner cap 50 and the laser probe body 20.

The inner cap 50 comprises a centrally positioned ventilator 70 for creating a flow 72 from the intake 66 of the inlet channel 64 through the heat channel 60 and out of the exhaust 62.

The ventilator 70 has a not shown means for connecting with power.

The arrows only illustrate the general direction of the flow 72 as the flow 72 can be turbulent.

The outer cap 42 has a cone 48 facing the ventilator 70.

Figure 2:
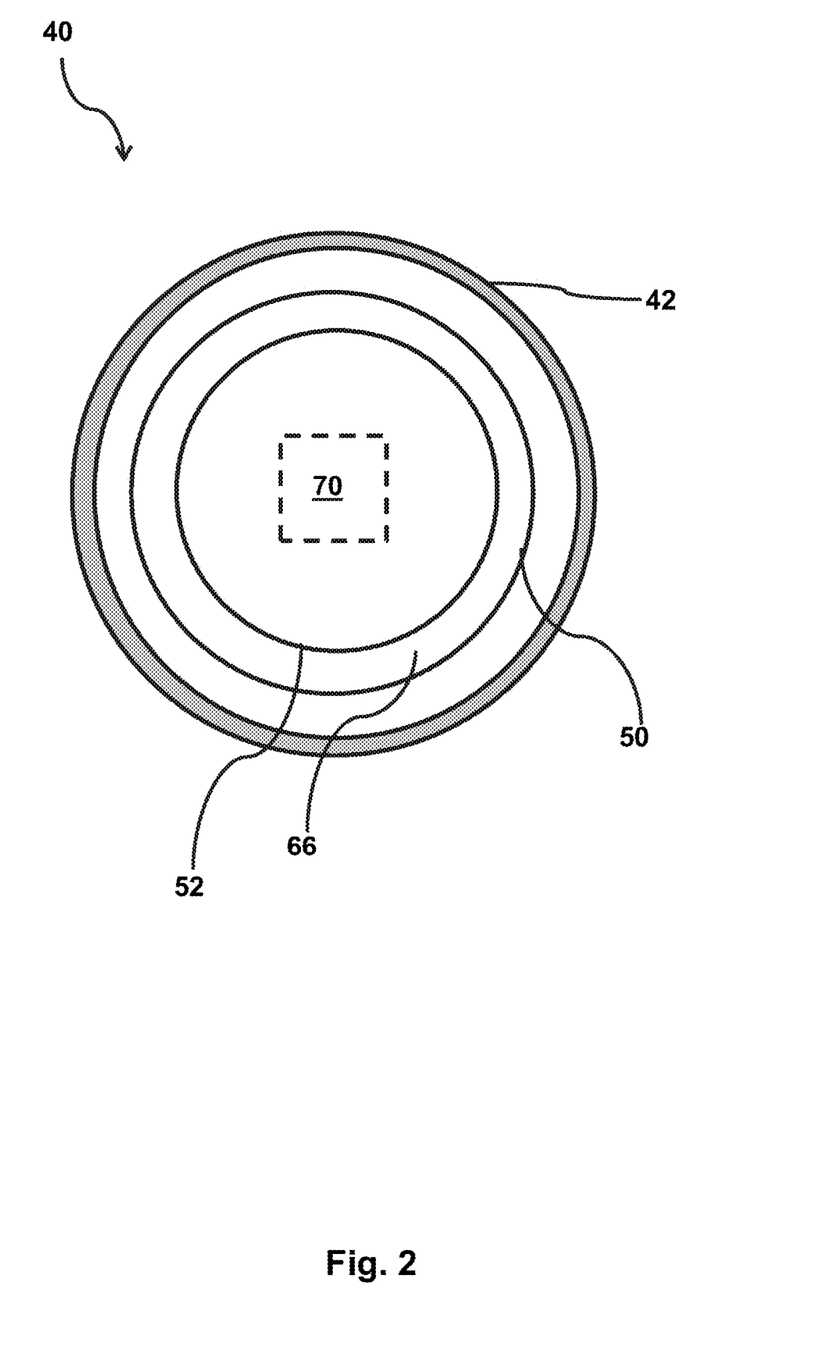
FIG. 2 illustrates a bottom view of a laser head.

FIG. 2 illustrates a bottom view of a laser head 40.

The bottom view discloses an outer cap 42 enclosing the rest of the laser head 40.

The outer cap 42 is followed by a not shown exhaust 62 enclosing the rest of the laser head 40.

The not shown exhaust 62 is followed by an inner cap 50 enclosing the rest of the laser head 40. The inner cap 50 has an extent which blocks for a bottom view of an exhaust 62, the extent ensures that less air circulates from the exhaust 62 to an intake 66.

The inner cap 50 is followed by the intake 66 enclosing the rest of the laser head 40.

The intake 66 is followed by a neck connection part 52.

The laser head 40 also has a ventilator 70.

Figure 3:
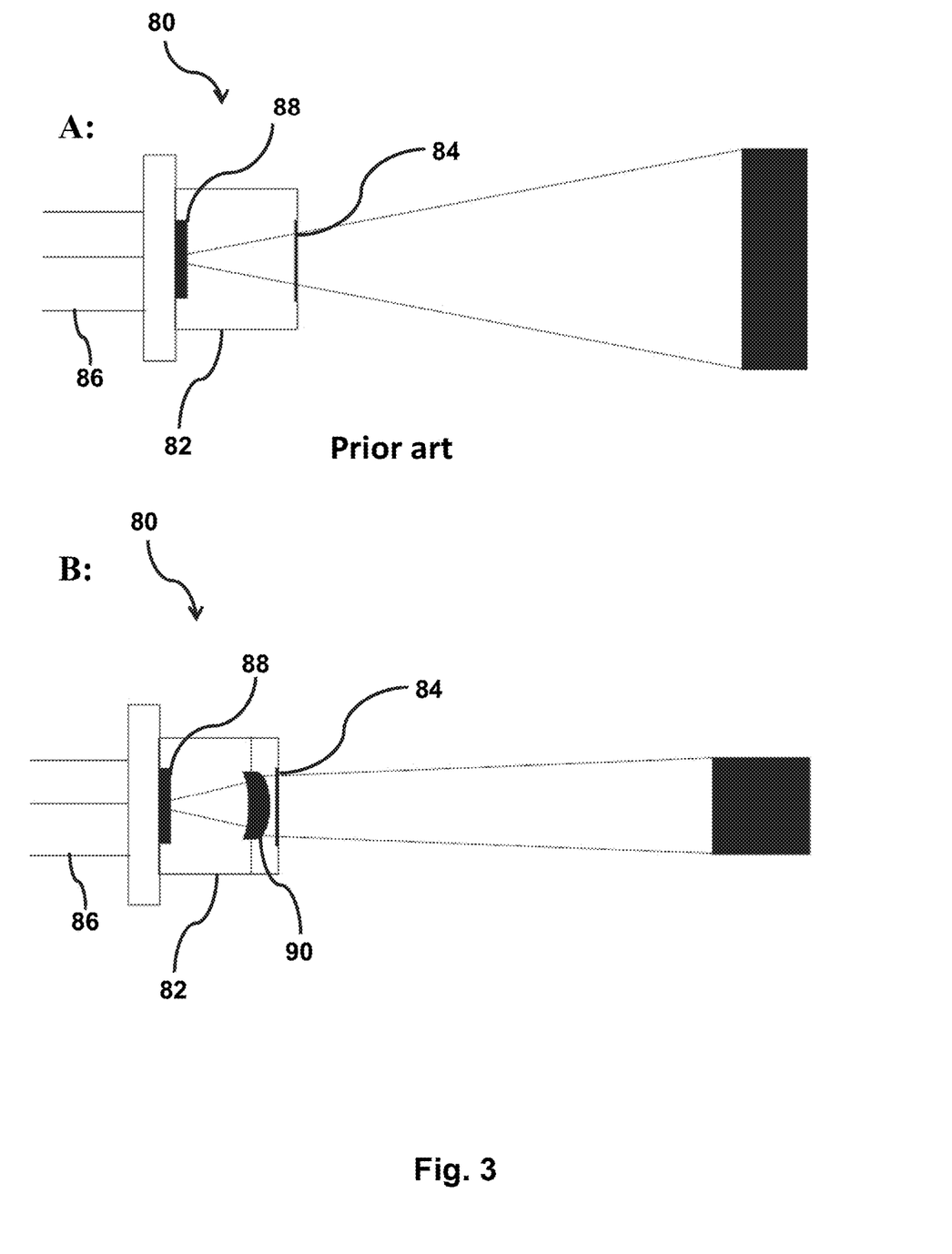
FIG. 3 illustrates a laser diode with and without an insert lens.

FIG. 3 illustrates a laser diode 80 with (B) and without (A) an insert lens 90.

FIG. 3A discloses a prior art laser diode 80 comprising an emitter 88, a housing 82 for the emitter, pins 86 for connecting with power, and a window 84 in front of the emitter 84. The prior art laser diode 80 will typically emit light with an angle of 10×30 degrees.

FIG. 3B discloses a laser diode 80 comprising an emitter 88, a housing 82 for the emitter, pins 86 for connecting with power, a window 84 in front of the emitter 84 and an insert lens 90 between the emitter 88 and the window 84. The laser diode 80 may emit light with an angle of 10×10 degrees, however this depends on the insert lens 90.

The laser diode 80 with the insert lens 90 could emit light having an angle of 15×15 degrees or any other angle.

Figure 4:
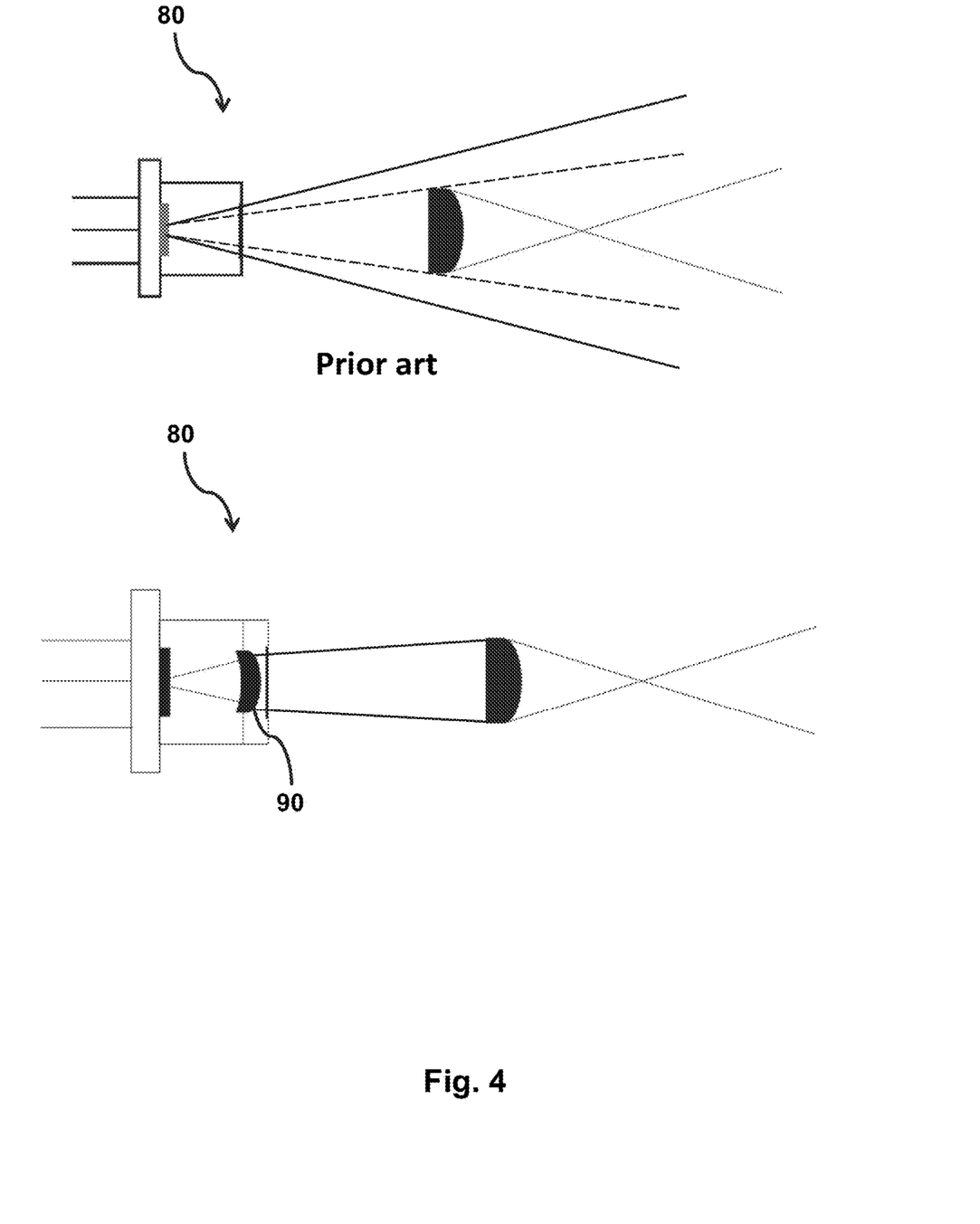
FIG. 4 illustrates a laser diode with and without an insert lens and with an external lens.

FIG. 4 illustrates a laser diode 80 with (B) and without (A) an insert lens 90 and with an external lens. FIG. 4A illustrates that a large part of the laser light is lost due to laser light not hitting the lens. FIG. 4B illustrates that the light is not lost due to the correction of the insert lens 90.

In practice, the setup shown in FIG. 4A will have a loss of 40%, when the external lens is positioned at a distance of 15 mm from the laser diode 80.

Figure 5:
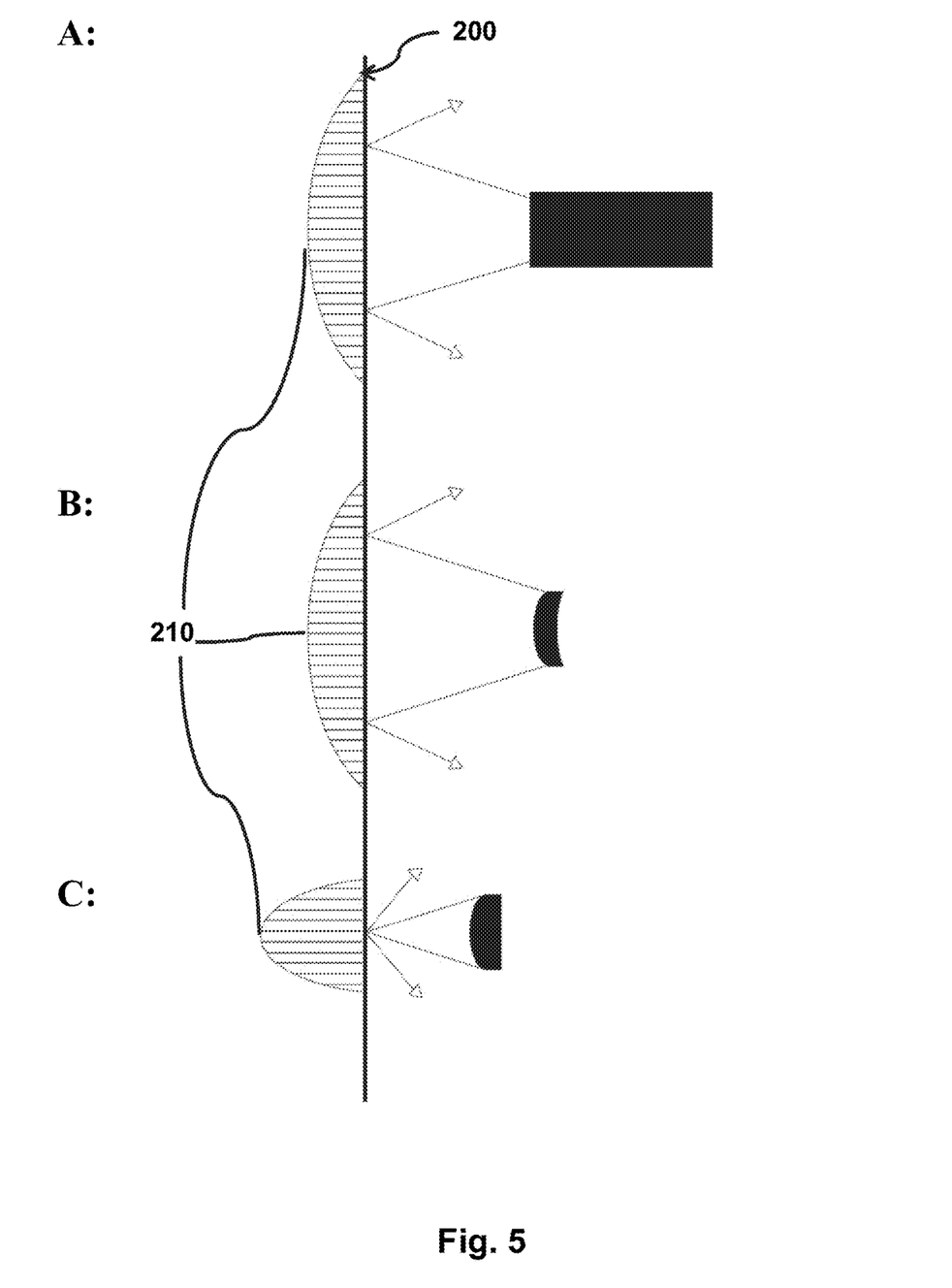
FIG. 5 illustrates skin penetration without direct skin contact.

FIG. 5 illustrates skin penetration 210 without direct skin contact.

The skin penetration 210 will only be superficial due to a large reflection from the skin if the laser lenses in FIG. 5A-C are not in direct contact with skin 200.

The fibre rod (FIG. 5A) and divergent lens (FIG. 5B) must be used at a distance if the intensity is larger than 500 mW/cm$^2$ at the skin in order to avoid burn in the tissue.

If a burn is wanted, a converging lens (FIG. 5C) is used such that the laser intensity can become large enough to cause a burn. This can be used for burning of tissue, e.g. plantar wart or corn.

Figure 6:
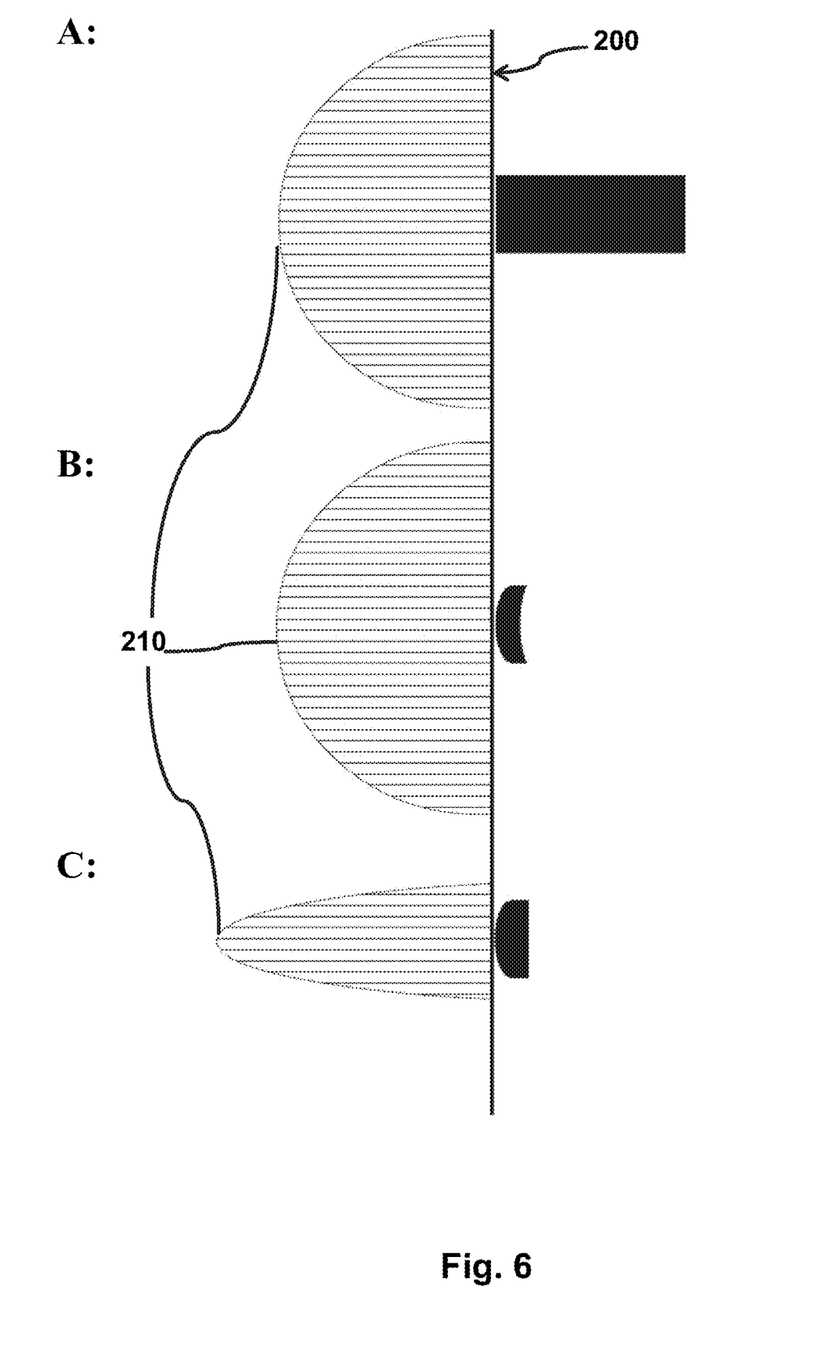
FIG. 6 illustrates skin penetration with direct skin contact.

FIG. 6 illustrates skin penetration 210 with direct skin contact.

The skin penetration 210 is significantly larger here than that in FIG. 5, because the skin reflects less when the lenses are in direct contact with the skin 200.

The fibre rod (FIG. 5A) and the divergent lens (FIG. 5B) will both have a wide skin penetration 210.

The converging lens (FIG. 5C) will surprisingly not cause a local burn in the tissue as the skin/tissue will disperse the laser light, but the converging lens will have a larger degree of skin penetration 210 compared to the fibre rod and the divergent lens.

Figure 7:
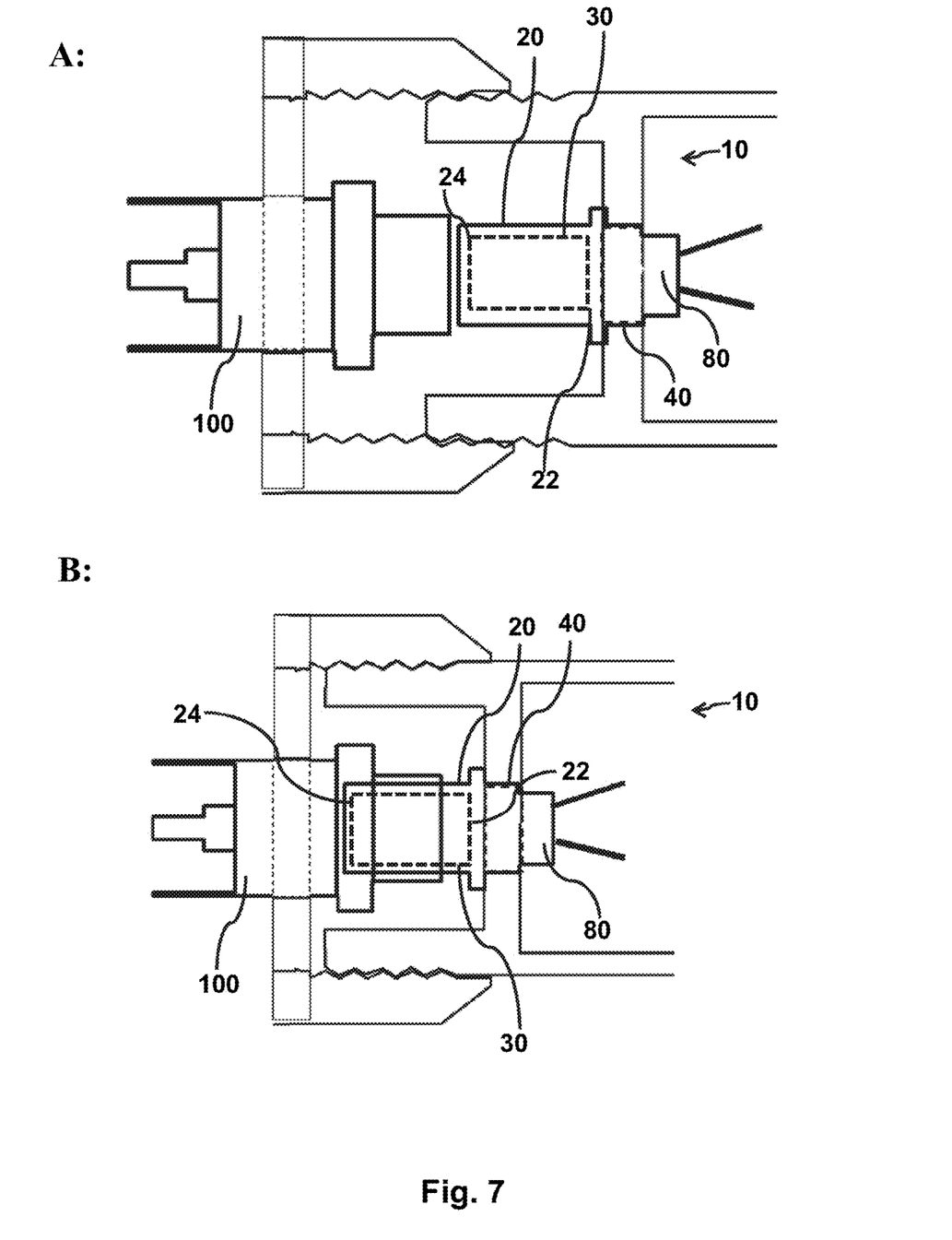
FIG. 7 illustrates a battery connecting with a laser probe.

FIG. 7 illustrates a battery 100 connecting with a laser probe 10. The laser probe 10 comprises a laser head 40 including a laser diode 80, a body 20, and a controller 30 positioned within the body 20. The controller 30 comprises a first connector 22 for connecting with the laser head 40, and a second connector 32 for connection with a battery 100. The battery 100 and the laser probe 10 have complementary threads to ensure good mechanical connection between the battery 100 and laser diode 10.

In FIG. 7B the battery 100 and the laser probe 10 are connected. The thread makes it easy for a user to disconnect and reconnect the battery 10 with the laser probe 10.

Figure 8:
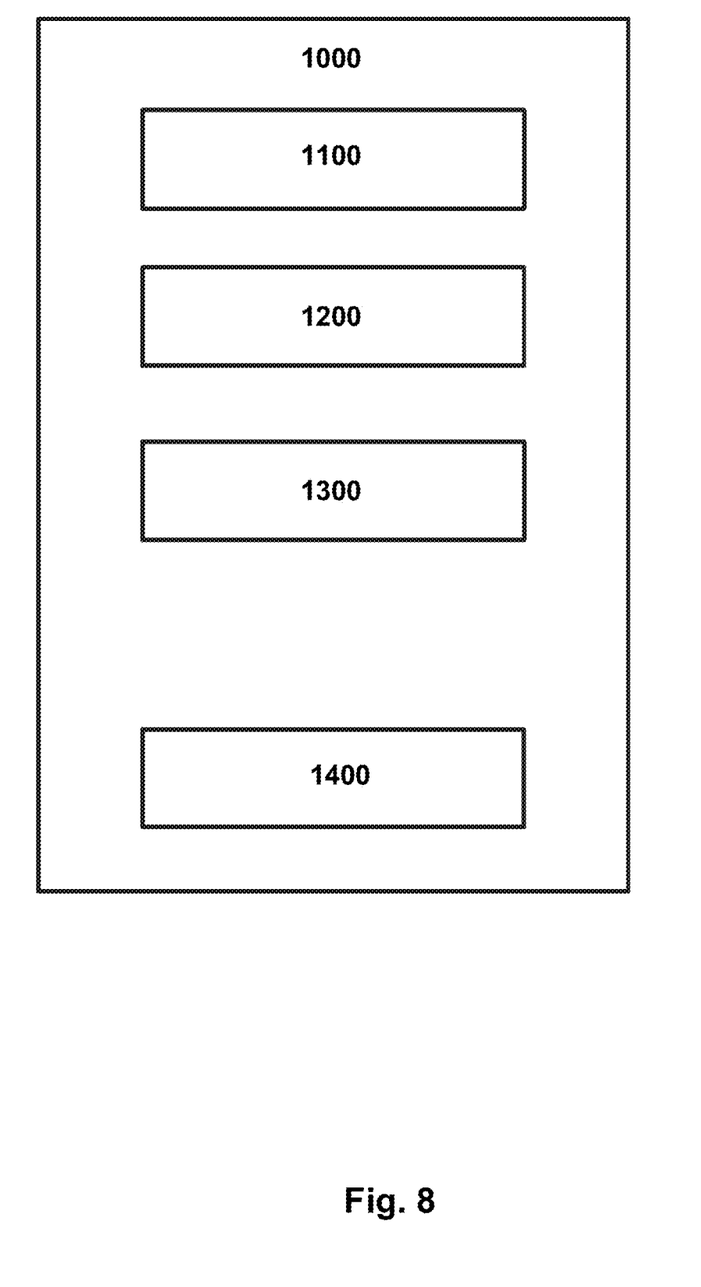
FIG. 8 illustrates a method of changing operational parameters of a laser probe.

FIG. 8 illustrates a method 1000 of changing the operational parameters of a laser probe 10. The method 1000 of changing operational parameters 110 of a laser probe 10 comprises one or more acts of:

an act of recognising 1100 a connection pattern 120 between the laser probe 10 and a battery 100;

an act of setting 1200 the laser probe 10 in a programmable mode 130; and an act of receiving 1300 instructions for changing the operational parameters 110 of the laser probe 10.

The method 1000 may further comprise an act of:

pairing 1400 the laser probe 10 with a remote 140 via Bluetooth™.

Figure 9:
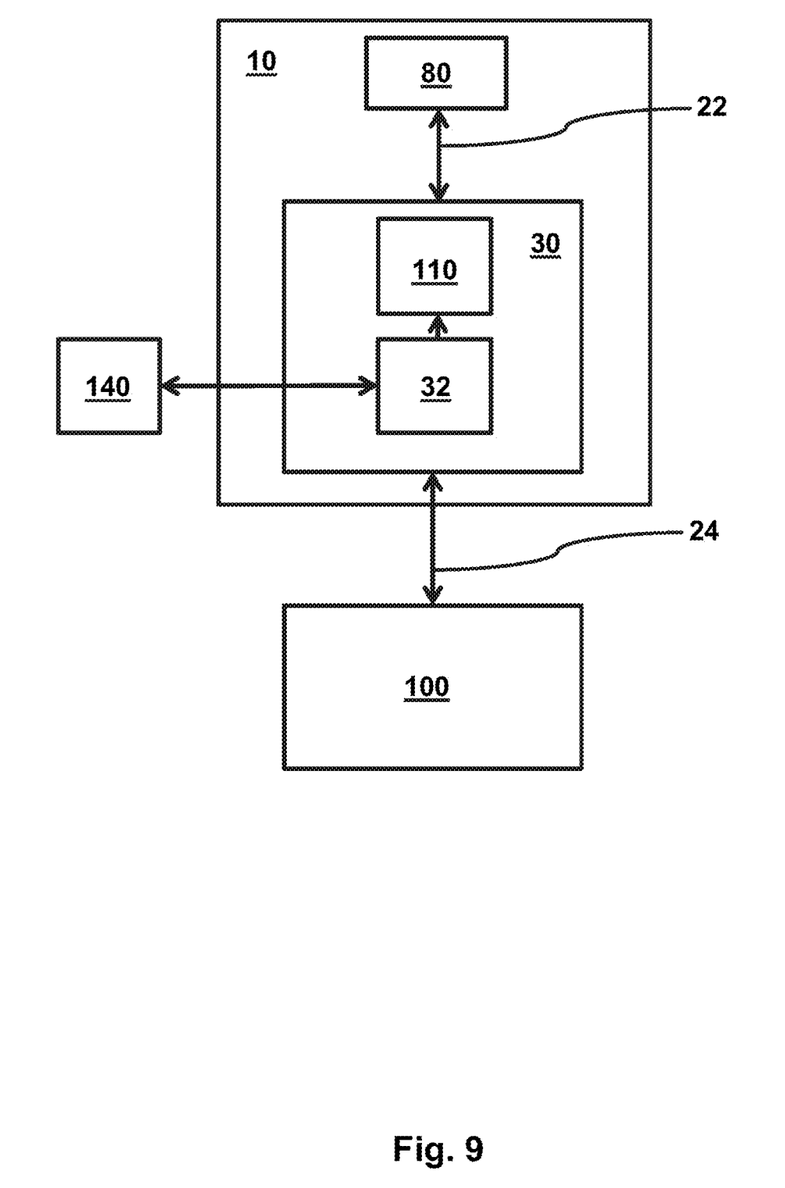
FIG. 9 illustrates a laser probe communicating with a remote.

FIG. 9 illustrates a laser probe 10 communicating with a remote 140. The laser probe 10 comprises a laser diode 80 and a connector 30. The connector comprises a first connector 22 connected to the laser diode 80, a second connector 24 for connection with a battery 100, a Bluetooth™ device 32 for paring with the remote 140, and operational parameters 110 stored on the controller determining the operation of the laser probe.

The remote 140 may be a smart phone, tablet, computer or any other electronic device capable of communicating with the laser probe 10 via Bluetooth™.

The laser probe 10 further comprises a battery 100, thereby making the laser probe 10 cordless.

Furthermore, the battery 100 enables a user to control the laser probe 10 without buttons as the controller 30 has means for recognizing a connection pattern between the battery 100 and laser probe 10.

The connection pattern could be connection, disconnection, connection within a short time period. If the controller 30 recognizes the connection pattern, then the Bluetooth™ device 32 will try to pair with a remote 140.

After pairing, the remote 140 can change the operational parameters 110 by sending instructions to the connector 30.

ITEM LIST

Item 1

A laser diode (80) for a low-level laser therapy (LLLT) laser probe (10), the laser diode (80) comprising an emitter (88), a housing (82) for protecting the emitter (88) having a window (84) for emission of light, pins (86) connected to the emitter (88) and an insert lens (90) positioned within the housing (82) between the emitter (88) and the window (84) for adjusting beam divergence.

Item 2

A laser diode (80) according to item 1, characterised in that the insert lens (90) is made of glass or plastic.

The invention claimed is:

1. A method of changing operational parameters of a laser probe comprising a body with one or more laser diodes, a controller having stored thereon operational parameters of the laser probe and a battery releasably connectable to the body, the method including the steps of:
   repeatedly and physically connecting and disconnecting the laser probe and the battery, wherein the controller performs the steps of:
   recognizing a connection pattern between the laser probe and the battery during the step of repeatedly and physically connecting and disconnecting, wherein the step of recognizing causes the controller to perform a step of setting the laser probe in a programmable mode; and
   while the laser probe is in the programmable mode, the controller performs a step of receiving instructions for changing the operational parameters of the laser probe.

2. The method according to claim 1, wherein the laser probe comprises sets of preset operational parameters stored on the controller, which can be shifted between by repeatedly and physically connecting and disconnecting the laser probe and the battery in accordance with the connection pattern.

3. The method according to claim 1, the method further including:
   a step of pairing the laser probe with a remote via Bluetooth™ communication protocol.

4. A laser probe for low-level laser therapy comprising:
   a body with one or more laser diodes;
   a battery releasably connectable to the body,
   a controller configured to measure a connection between the laser probe and the battery,
   the controller having stored thereon operational parameters, wherein the battery and the laser probe are configured for repeatedly and physically connecting and disconnecting, the controller being configured
   to recognize a physical connection pattern of the repeated and physical connection and disconnection between the laser probe and the battery and set the laser probe in a programmable mode as a function recognizing the physical connection pattern, wherein the controller receives instructions for changing the operational parameters of the laser probe.

5. The laser probe according to claim 4, wherein the controller includes a Bluetooth™ device configured and arranged to pair the laser probe with a remote via Bluetooth™ communication protocol.

6. The method according to claim 1, wherein the controller further performs the steps of changing the operational parameters of the laser probe based on the received instructions.

* * * * *